(12) United States Patent
Cook et al.

(10) Patent No.: US 6,983,548 B1
(45) Date of Patent: Jan. 10, 2006

(54) FOOT MEASUREMENT APPARATUS

(75) Inventors: Christopher Cook, Portland, OR (US); Bruce J. Kilgore, Lake Oswego, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 10/316,117

(22) Filed: Dec. 11, 2002

(51) Int. Cl.
*A43D 1/02* (2006.01)
*A61B 5/107* (2006.01)

(52) U.S. Cl. .......................... 33/515; 33/3 B
(58) Field of Classification Search ............. 33/515, 33/3 R, 4, 5, 6, 3 A, 3 B, 3 C, 549, 783, 33/806, 832, 512
See application file for complete search history.

(56) References Cited

U.S. PATENT DOCUMENTS

| 115,761 | A |   | 6/1871 | McNichol |  |
|---|---|---|---|---|---|
| 546,287 | A |   | 9/1895 | Adler |  |
| 770,065 | A |   | 9/1904 | Hertzler et al. |  |
| 967,464 | A | * | 8/1910 | Tilles | 33/3 R |
| 1,221,557 | A | * | 4/1917 | Madden | 33/3 R |
| 1,359,375 | A | * | 11/1920 | Hine | 33/3 B |
| 1,507,539 | A | * | 9/1924 | Wheeler | 33/3 B |
| 1,525,064 | A | * | 2/1925 | Brown | 33/3 A |
| 1,568,072 | A |   | 1/1926 | Krueger et al. |  |
| 1,837,809 | A |   | 12/1931 | Delhaye |  |
| 2,163,661 | A | * | 6/1939 | Brown | 33/3 R |
| 2,507,032 | A |   | 5/1950 | Mantos |  |
| 2,522,899 | A |   | 9/1950 | Schlaugh et al. |  |
| 2,842,344 | A |   | 11/1958 | Brannock |  |
| 3,438,134 | A |   | 4/1969 | Schunk |  |
| 3,457,647 | A |   | 7/1969 | Cohen et al. |  |
| 3,579,837 | A |   | 5/1971 | Soriano |  |
| 4,520,581 | A |   | 6/1985 | Irwin et al. |  |
| 4,635,366 | A |   | 1/1987 | Fohrman et al. |  |
| 4,939,849 | A | * | 7/1990 | Johnson | 33/811 |
| 5,101,568 | A |   | 4/1992 | Ferragamo |  |
| 5,164,793 | A |   | 11/1992 | Wolfersberger et al. |  |
| 5,671,055 | A |   | 9/1997 | Whittlesey et al. |  |
| 5,822,223 | A |   | 10/1998 | Genest |  |
| 6,029,358 | A |   | 2/2000 | Mathiasmeier et al. |  |
| 6,163,971 | A |   | 12/2000 | Humphries, Jr. et al. |  |
| 6,192,593 | B1 |   | 2/2001 | Borchers et al. |  |
| 6,226,881 | B1 |   | 5/2001 | Landauer |  |
| 6,256,896 | B1 |   | 7/2001 | Landauer |  |
| 6,331,893 | B1 |   | 12/2001 | Brown et al. |  |
| 2003/0033723 | A1 |   | 2/2003 | Snook |  |

OTHER PUBLICATIONS

Children's Home Shoe Sizer, Copyright 2000, One Step Ahead®, 1 page.
The Genuine Brannock Device, The Brannock Device Co. Inc., Apr. 29, 2001, 7 pages.

* cited by examiner

*Primary Examiner*—Christopher W. Fulton
(74) *Attorney, Agent, or Firm*—Banner & Witcoff, Ltd.

(57) ABSTRACT

The invention is a foot measurement apparatus suitable for mailing to individuals. The measurement apparatus includes a base with a scale, a first abutment attached to the base, and a second abutment that is movably-attached to the base. In an assembled configuration, the first and second abutments extend outward from the base and contact the foot to measure, for example, the length or width of the foot. In a collapsed configuration, however, the first and second abutments collapse against the base in order to decrease the size of the measurement apparatus, thereby facilitating mailing.

13 Claims, 8 Drawing Sheets

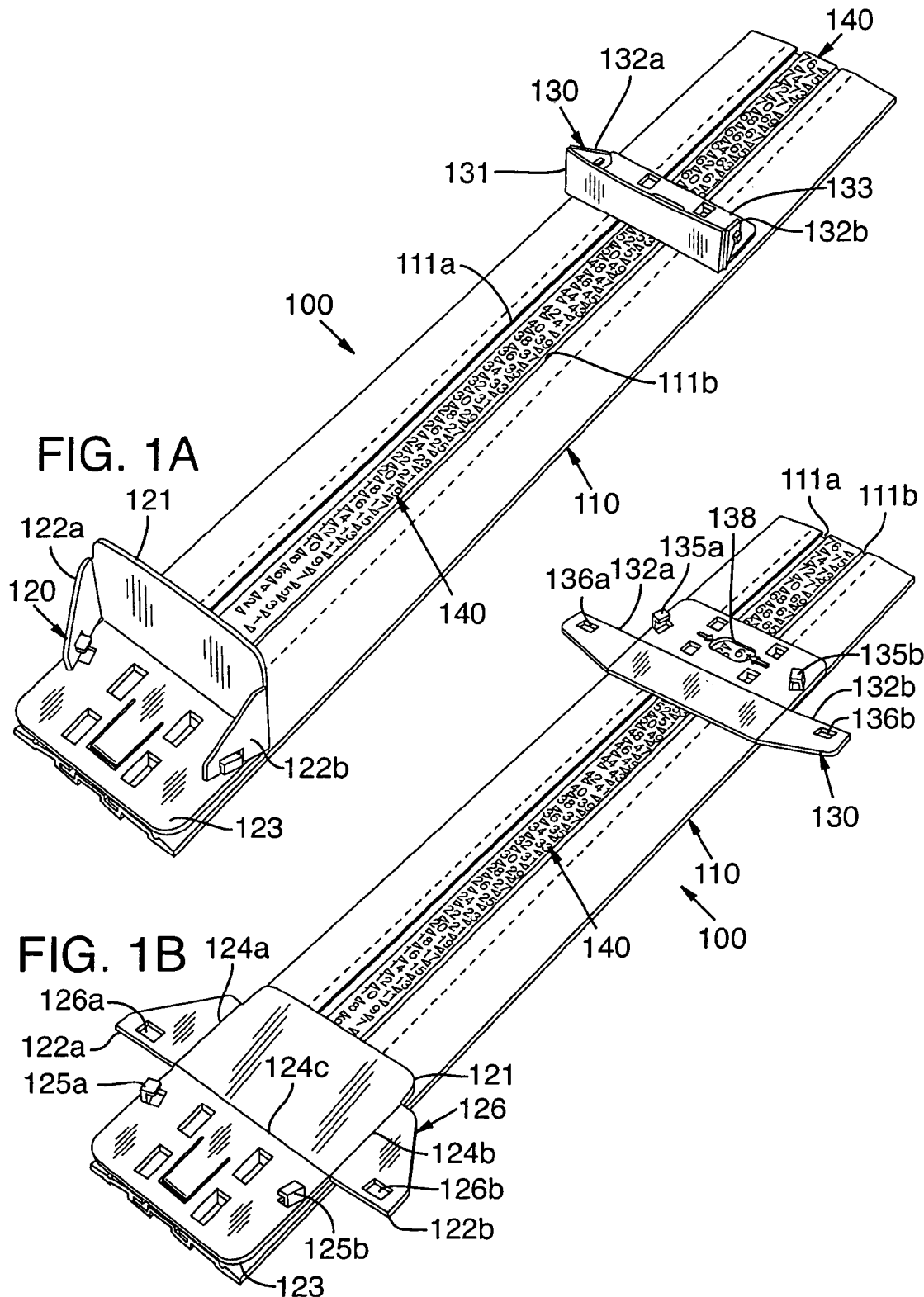

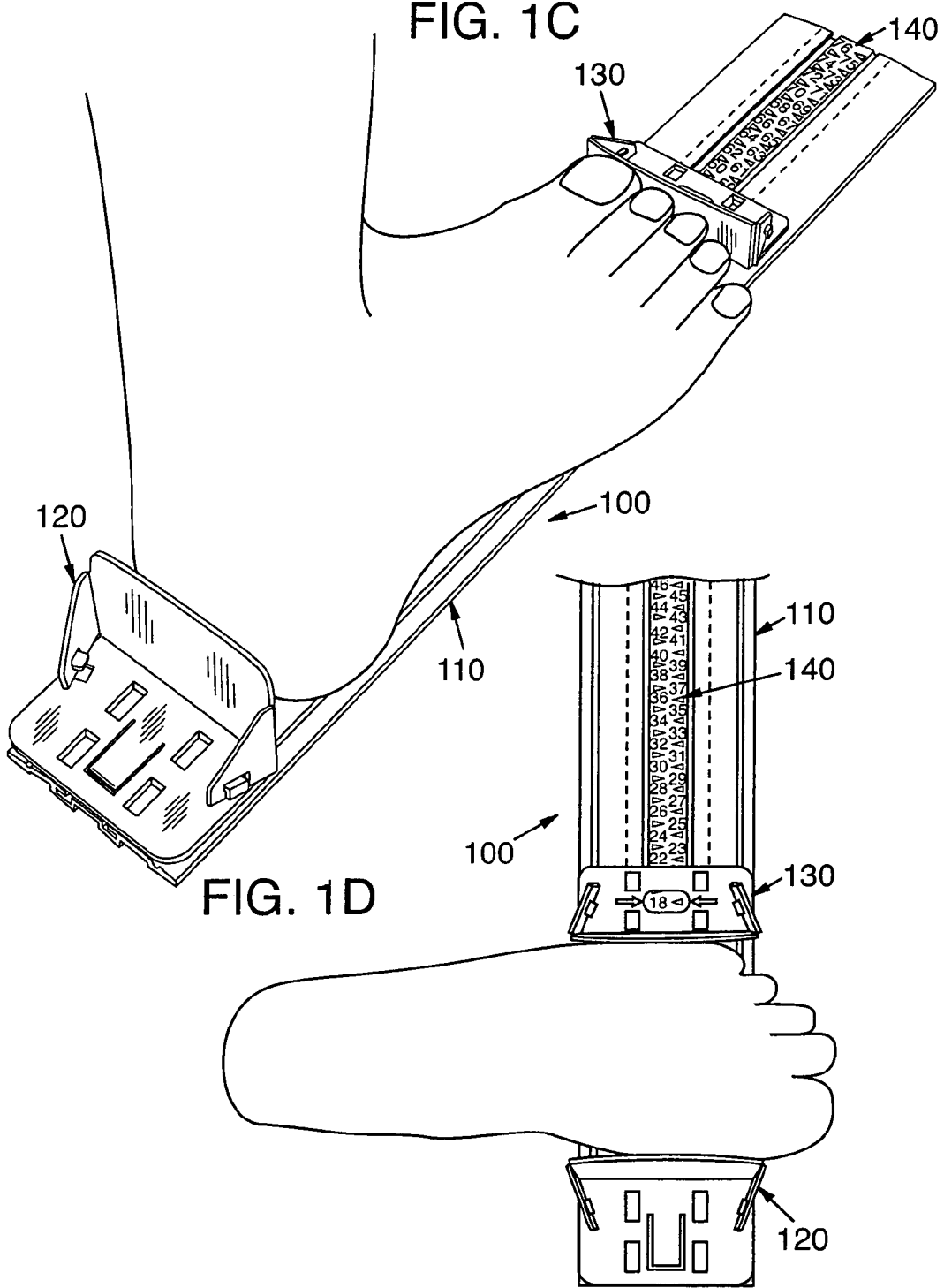

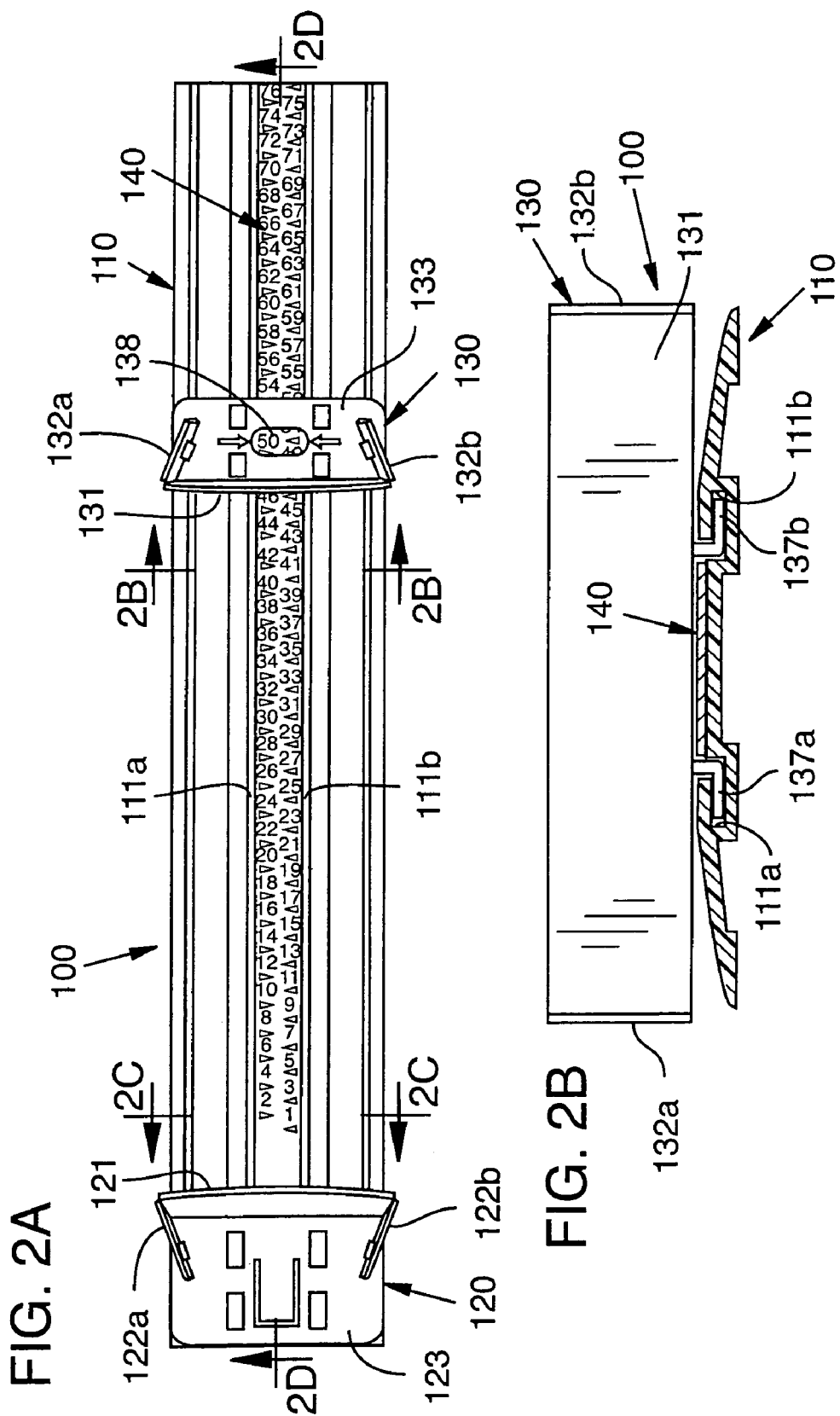

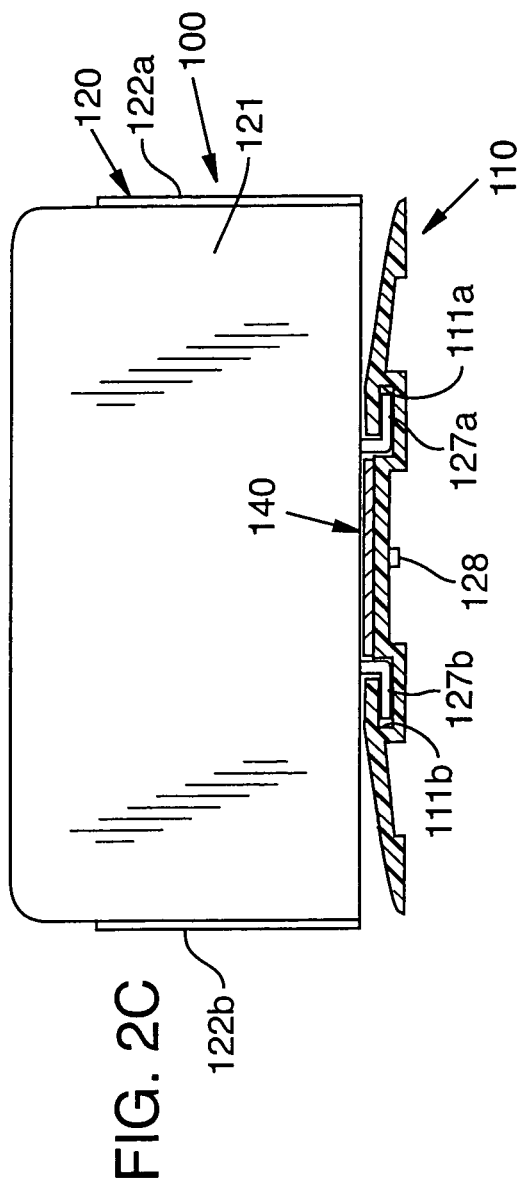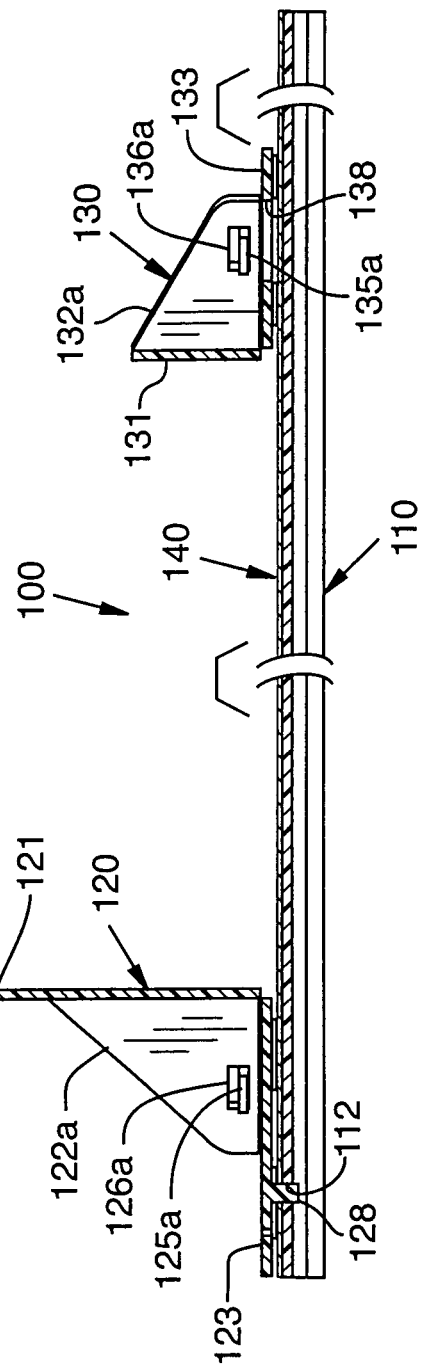

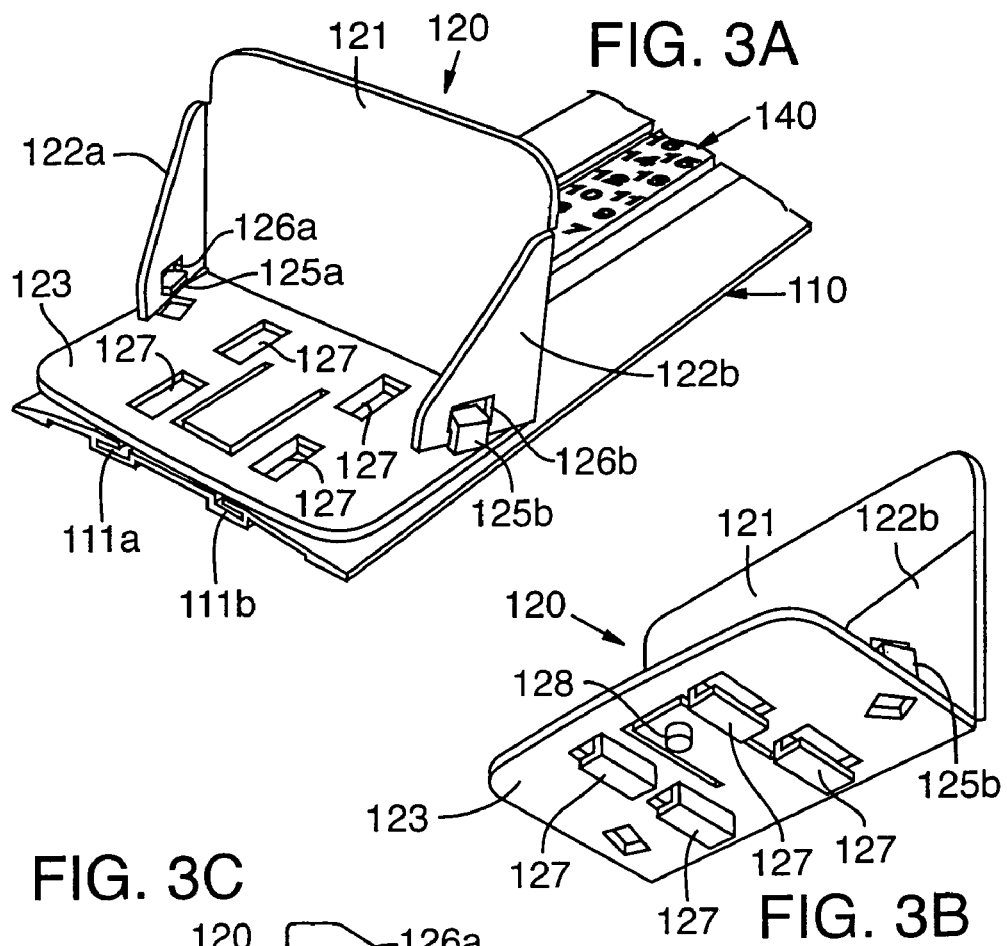
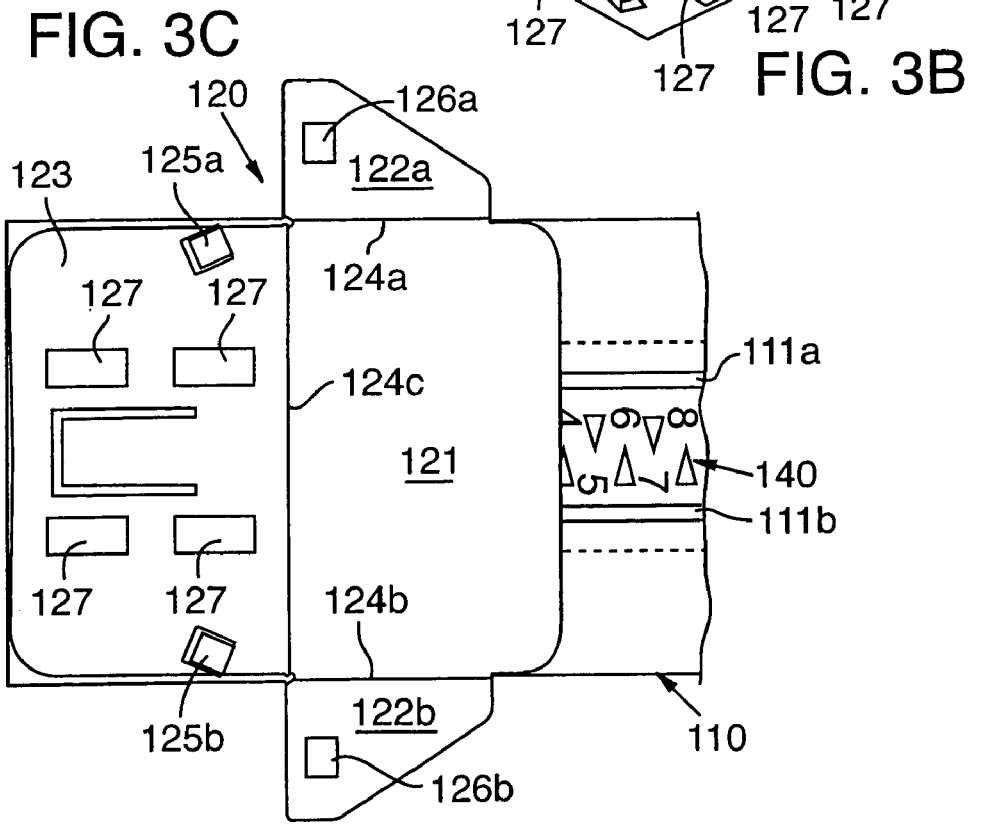

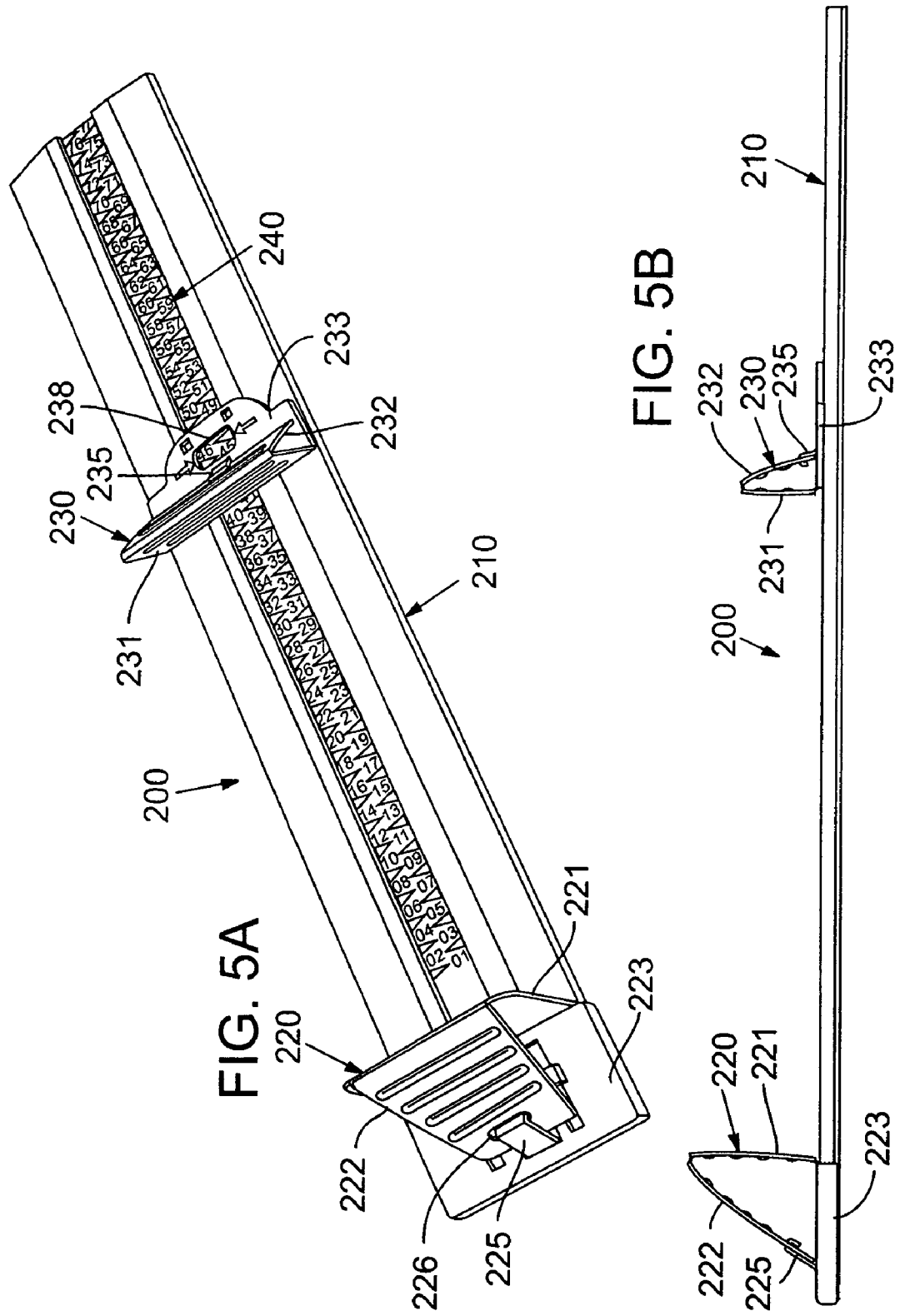

FOOT MEASUREMENT APPARATUS

BACKGROUND OF THE INVENTION

1. Field of the Invention

The present invention relates to an apparatus for measuring dimensions of a foot, particularly length and width. The invention concerns, more specifically, a lightweight and collapsible foot measuring apparatus that is suitable for mailing to individuals.

2. Description of Background Art

Although sizing systems for footwear are standardized, many individuals find that footwear sizes vary between manufacturers. Consequently, an individual who wears a first size of footwear from a first manufacturer may wear a second size of footwear from a second manufacturer, with both the first size and the second size providing the individual with a proper fit. The primary reason for inconsistencies between footwear sizes relates to the unique lasts utilized by different manufacturers to produce footwear. In shaping lasts for the manufacture of mass-produced footwear, foot measurements from a broad spectrum of the population are utilized to derive a set of dimensions that theoretically comprise a statistically-average foot for each shoe size. The dimensions may include the overall length of the foot, width of the foot, height of the first digit, contour of the instep, and at least six girth measurements. The dimensions are then used by the manufacturer to shape a corresponding series of lasts. Variations between the lasts used by different manufacturers result in footwear with different fit properties. Accordingly, the size of footwear worn by an individual may vary depending upon the manufacturer that produced the footwear.

A significant portion of modern footwear sales are conducted via mail order through catalogs or the Internet. Mail order provides a convenient manner for individuals to purchase footwear, especially if specific brands or styles are not offered by merchants in the geographic locale of the individual. A recurring issue with regard to mail order footwear sales relates to sizing. When purchases are made at a retail footwear outlet, the individual is typically provided with the opportunity to test-fit footwear prior to the sale.

In this manner, the individual is assured that the footwear will fit properly. When sales occur through mail order, however, the customer rarely has the opportunity to test-fit the footwear prior to placing the order. Consequently, the individual may be required to return the footwear and place a substitute order if the ordered size does not provide a proper fit.

Proper sizing is also an issue for team sales. Sporting organizations often acquire footwear from a common manufacturer, thereby assuring a uniform appearance among team members. In order to ensure that the proper size of footwear is ordered for each team member, foot measurements for each individual may be taken. A common foot measuring device is the Brannock Device, which is found in many conventional retail footwear outlets. The Brannock Device includes a fixed scale, a first sliding scale and a second sliding scale. To determine foot size, the user compares readings from the fixed scale, which determines the overall length of the foot, and the first sliding scale, which determines the position of the ball of the foot. The greater reading typically indicates foot size. In addition, foot width may be measured using the second sliding scale.

A common issue with foot measuring systems such as the Brannock Device relates back to inconsistencies in footwear sizes provided by different manufacturers. Although the Brannock Device is well-suited for use in retail footwear outlets to provide an approximate footwear size, the Brannock Device may not be accurate with respect to individual manufacturers. Accordingly, reliance upon the Brannock Device, or any other device not calibrated to a specific manufacturer, may result in mail ordered footwear that is improperly fitted.

In order to provide a measurement system that is calibrated to a specific manufacturer, many manufacturers provide foot sizing charts that may be downloaded from the Internet and printed. To use the charts, the individual aligns the foot with a scale on the chart and reads the appropriate size. Printable charts, however, may not be precisely calibrated due to inherent inaccuracies in the printing process. To adjust for the inaccuracies, instructions accompanying the chart often provide means for calibrating the chart.

Accurate calibration, however, is often difficult to achieve.

SUMMARY OF THE INVENTION

The present invention provides a lightweight and collapsible foot measurement apparatus that may be mailed to an individual, thereby providing the individual with an accurate means for determining proper footwear size from measurements of both the length and width of the foot.

The measurement apparatus includes a base, a scale, a stationary element, and a translating element. The scale is positioned on the base. The stationary element is connected to the base and has a fixed position with respect to the scale. The translating element is movably-connected to the base and has a variable position with respect to the stationary element and the scale. The stationary element and the translating element extend outward from the base to place the measurement apparatus in an assembled configuration, and either the stationary element or the translating element are collapsible to place the measurement apparatus in a collapsed configuration. The measurement apparatus, therefore, has a lesser size in the collapsed configuration than in the assembled configuration.

The lesser size facilitates mailing of the measurement apparatus. Whereas a box or other bulky mailing container would be necessary for the measurement apparatus when in the assembled configuration, an envelope or other inexpensive mailing container may be utilized for the measurement apparatus when in the collapsed configuration.

The measurement apparatus may be utilized to measure both the length and width of the foot, for example. The first portion of the foot may be placed against the first abutment and then the second abutment may be moved until it abuts the second portion of the foot. Whether the first and second portion are the heel and toes or the sides of the foot, dimensions of the foot may be read from the scale.

The advantages and features of novelty characterizing the present invention are pointed out with particularity in the appended claims. To gain an improved understanding of the advantages and features of novelty, however, reference may be made to the following descriptive matter and accompanying drawings that describe and illustrate various embodiments and concepts related to the invention.

DESCRIPTION OF THE DRAWINGS

The foregoing Summary of the Invention, as well as the following Detailed Description of the Invention, will be better understood when read in conjunction with the accompanying drawings.

FIG. 1A is a perspective view of a first foot measurement apparatus in accordance with the present invention, the first foot measurement apparatus being in an assembled configuration.

FIG. 1B is a perspective view of the first foot measurement apparatus, as depicted in FIG. 1A, the first foot measurement apparatus being in a collapsed configuration.

FIG. 1C is a perspective view of the first foot measuring apparatus depicting a foot positioned for a length measurement.

FIG. 1D is a top plan view of the first foot measuring apparatus depicting a foot positioned for a width measurement.

FIG. 2A is a top plan view of the first foot measurement apparatus.

FIG. 2B is a first cross-sectional view of the first foot measurement apparatus, as defined by line 2B—2B in FIG. 2A.

FIG. 2C is a second cross-sectional view of the first foot measurement apparatus, as defined by line 2C—2C in FIG. 2A.

FIG. 2D is a third cross-sectional view of the first foot measurement apparatus, as defined by line 2D—2D in FIG. 2A.

FIG. 3A is a first perspective view of a stationary element of the first foot measurement apparatus.

FIG. 3B is a second perspective view of the stationary element of the first foot measurement apparatus.

FIG. 3C is a top plan view of the stationary element in the collapsed configuration.

FIG. 5A is a perspective view of a second foot measurement apparatus in accordance with the present invention, the second foot measurement apparatus being in an assembled configuration.

FIG. 5B is a side elevational view of the second foot measurement apparatus in the assembled configuration.

DETAILED DESCRIPTION OF THE INVENTION

Figure 4A:
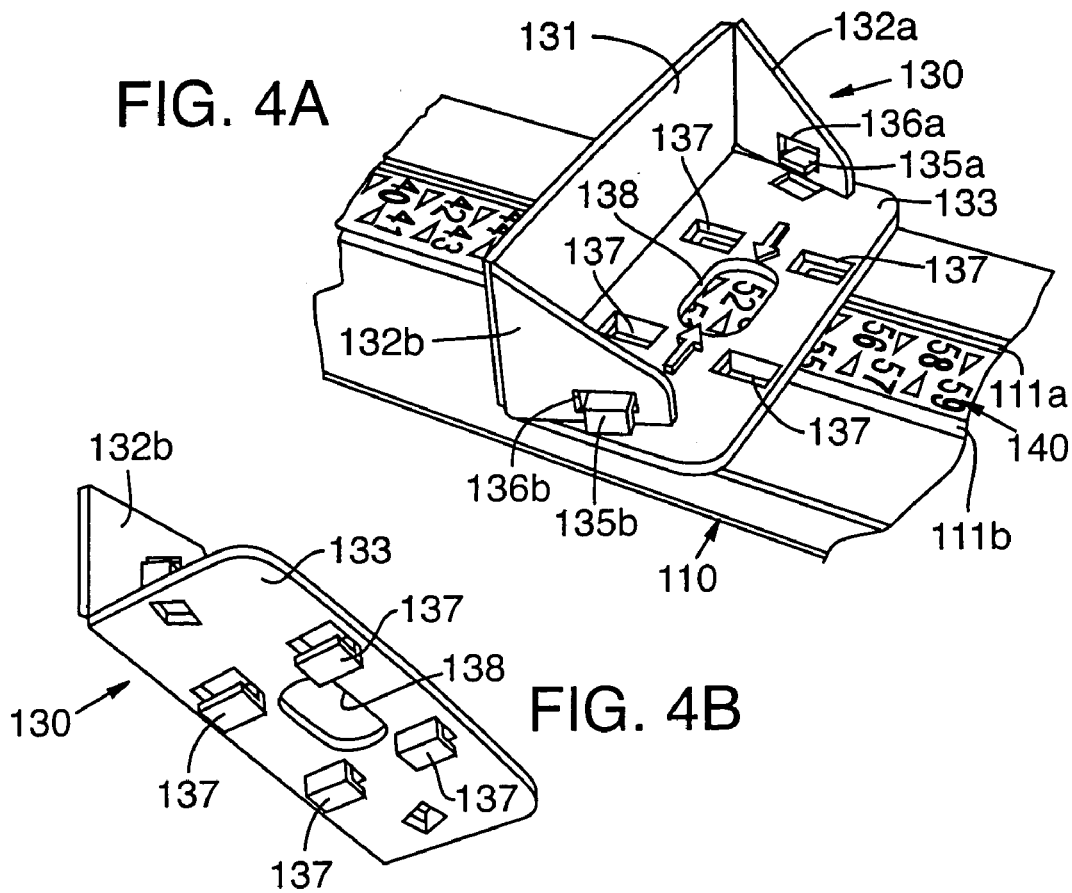
FIG. 4A is a first perspective view of a translating element of the first foot measurement apparatus.
Figure 4B:
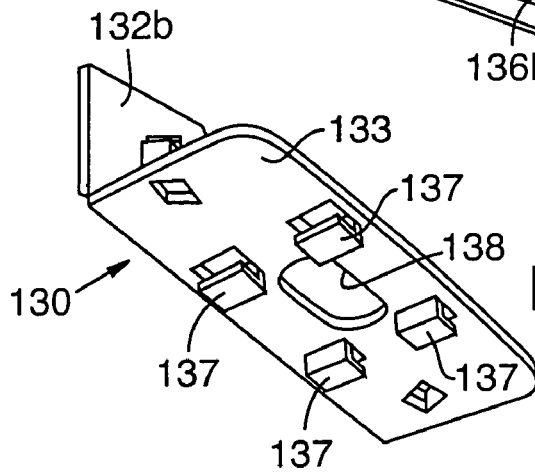
FIG. 4B is a second perspective view of the translating element of the first foot measurement apparatus.
Figure 4C:
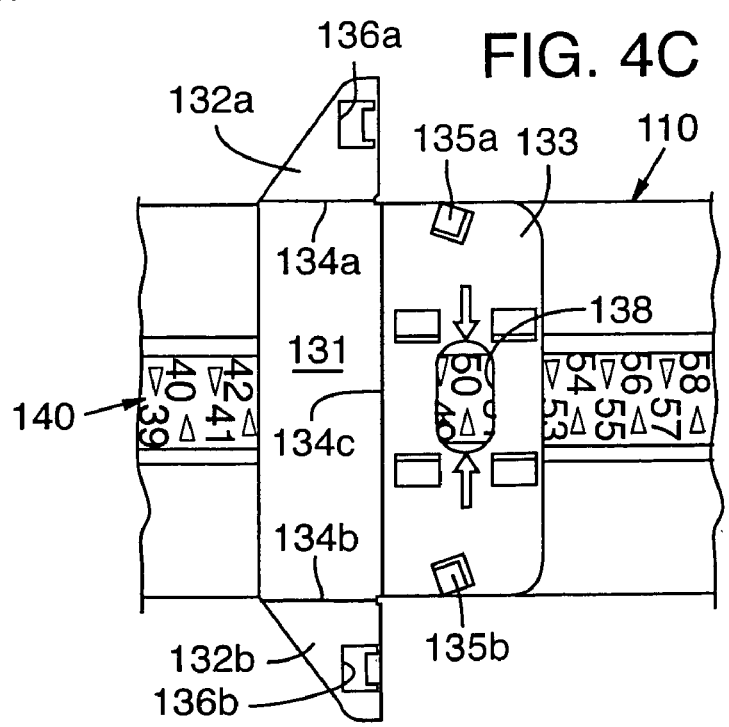
FIG. 4C is a top plan view of the translating element in the collapsed configuration.

Referring to the figures, wherein like numerals indicate like elements, a foot measurement apparatus 100 and a foot measurement apparatus 200 in accordance with the present invention are disclosed. Measurement apparatuses 100 and 200 are lightweight and collapsible devices that may be mailed to an individual who intends to purchase footwear through mail order or through the Internet, for example. Prior to ordering the footwear, the individual may utilize one of measurement apparatuses 100 and 200 to measure both the length and the width of a foot, thereby ensuring that ordered footwear is properly fitted to each individual. Following use, measurement apparatuses 100 and 200 may be retained by the individual for a future use or disassembled and recycled. In addition to individuals, measurement apparatuses 100 and 200 may be utilized by sporting organizations to properly fit footwear to a plurality of individuals.

The capacity for easily and inexpensively mailing one of measurement apparatuses 100 and 200 to an individual is enhanced by the lightweight and collapsible nature of measurement apparatuses 100 and 200.

The features and operation of measurement apparatus 100 will now be discussed in detail.

Measurement apparatus 100 is depicted in FIGS. 1–4 and includes four primary components: a base 110, a stationary element 120, a translating element 130, and a scale 140. Although the various components may be manufactured from a plurality of materials, decreased weight is achieved by forming the components from polymers. In an assembled configuration, which is depicted in FIG. 1A, stationary element 120 and translating element 130 protrude upward from base 110. The mailing volume may be reduced from the assembled configuration by placing measurement apparatus 100 in a collapsed configuration wherein stationary element 120 and translating element 130 are disassembled and collapsed against base 110, as depicted in FIG. 1B. In the collapsed configuration, measurement apparatus 100 may be placed within a standard mailing envelope and shipped to an individual. Directions that accompany measurement apparatus 100 may instruct the individual in the manner of placing measurement apparatus 100 in the assembled configuration. In addition, the directions may provide information relating to the use of measurement apparatus 100 and the process of ordering footwear once measurements of the foot are ascertained.

In order to accurately ascertain foot measurements, a foot is positioned on base 110 and between stationary element 120 and translating element 130 such that the heel of the foot abuts stationary element 120. Translating element 130, which may be moved along base 110, is then positioned in an abutting relationship with the toes of the foot, as depicted in FIG. 1C. A length measurement corresponding with the length of the foot may then be determined by reference to the position of translating element 130 in relation to scale 140. Once the length measurement is accurately determined, the foot is rotated 90 degrees such that a side portion of the foot abuts stationary element 120. Translating element 130 is then positioned in an abutting relationship with an opposite side of the foot, as depicted in FIG. 1D. A width measurement corresponding with the width of the foot is then determined by reference to the position of translating element 130 in relation to scale 140. The manner in which measurement apparatus 100 may be utilized to ascertain foot measurements will be better understood based upon the following discussion regarding the individual components of measurement apparatus 100.

Base 110 forms a substrate that permits stationary element 120, translating element 130, and scale 140 to interact in the manner described above, thereby facilitating foot measurements, and may have a variety of configurations within the scope of the present invention. As depicted in the figures, however, base 110 is formed as a generally planar member that provides measurement apparatus 100 with a lightweight, compact design suitable for mailing. In addition, the planar configuration of base 110 provides a generally level upper surface that the foot is placed upon when ascertaining foot measurements.

The upper surface of base 110 includes a first channel 111a and a second channel 111b that extend in parallel along both sides of scale 140. Channels 111 are configured to receive translating element 130, permit translating element 130 to slide along the longitudinal length of base 110, and prevent translating element 130 from becoming separated from base 110. Channels 111, therefore, are configured to direct the sliding movement of translating element 130 in relation to scale 140. In cross-section, channels 111 may each have an L-shape, as depicted in FIGS. 2B and 2C, that receives a corresponding portion of translating element 130, as described below. Alternately, channels 111 may be replaced by a single channel that has a dovetail configuration, for example. Translating element 130 would then have a modified configuration that corresponds with the dovetail-shaped channel to permit translating element 130 to slide along base 110 and in relation to scale 140.

Base 110 also includes a positioning aperture 112 that provides a reference position for attaching stationary element 120 and locating scale 140. The function and manner of utilizing positioning aperture 112 will be described in greater detail below.

Stationary element 120 is securely positioned on an end of base 110. When measurement apparatus 100 is in the assembled configuration, stationary element 120 extends upward from base 110, as depicted in FIGS. 1A and 3A, and provides a stationary location that abuts either the heel or the side of the foot when ascertaining foot measurements. When measurement apparatus 100 is in the collapsed configuration, stationary element 120 is collapsed against base 110, thereby having a low profile as depicted in FIGS. 1B and 3C.

The primary elements of stationary element 120 are an abutment portion 121, a pair of support portions 122a and 122b, and a connection portion 123. Abutment portion 121 directly contacts the foot and provides a stationary and secure abutment for the foot when measuring length or width. Support portions 122 extend backward from abutment portion 121 to provide support against backward pressure from the foot. Connection portion 123 provides a secure connection between stationary element 120 and base 110.

Stationary element 120 is manufactured as a generally flat element having a plurality of flexion lines 124 that separate portions 121, 122, and 123 from each other. Flexion lines 124 are located as follows: flexion line 124a is positioned between abutment portion 121 and support portion 122a; flexion line 124b is positioned between abutment portion 121 and support portion 122b; and flexion line 124c is positioned between abutment portion 121 and connection portion 123. Flexion lines 124 permit portions 121, 122, and 123 to be bent in relation to each other. More specifically, flexion lines 124 act as hinges that permit portion 121, 122, and 123 to flex or rotate relative to each other, thereby placing measurement apparatus 100 in either the collapsed configuration or the assembled configuration. When stationary element 120 is formed from a polymer material, flexion lines 124 may be lines of reduced thickness that facilitate bending along the lines. In alternate embodiments, flexion lines 124 may be hinges or other devices that permit bending along predetermined lines.

Measurement apparatus 100 is generally manufactured and mailed in the collapsed configuration. Following receipt of measurement apparatus 100, the individual may reconfigure measurement apparatus 100 to be in the assembled configuration. With respect to stationary element 120, the individual will bend support portions 122a and 122b along flexion lines 124a and 124b, respectively. Simultaneously, the individual will bend abutment portion 121 along flexion line 124c until a pair of tabs 125a and 125b that are formed on connection portion 123 engage a pair of tab apertures 126a and 126b, respectively, which are formed in support portions 122a and 122b. That is, stationary element 120 may be changed from the collapsed configuration to the assembled configuration by merely bending stationary element 120 along the various flexion lines 124 and engaging tabs 125 with tab apertures 126. Similarly, stationary element 120 may be changed from the assembled configuration to the collapsed configuration by disengaging tabs 125 from tab apertures 126, and then returning the various portions 121, 122, and 123 to a generally flat relationship.

Stationary element 120 is securely attached to base 110 through connection portion 123. Within the scope of the present invention, a plurality of methods may be utilized to attach stationary element 120 to base 110, including adhesives and heat bonding, for example. As depicted, however, connection portion 123 includes inserts 127 and a positioning protrusion 128. As discussed above, base 110 includes two channels 111 that have an L-shaped cross-section. Inserts 127 each have a corresponding L-shape that fits within channels 111. In order to prevent stationary element 120 from sliding along channels 111, positioning protrusion 128 engages positioning aperture 112 in base 110. Inserts 127 and positioning protrusion 128, therefore, cooperatively operate to securely attach stationary element 120 to base 110.

Translating element 130 has a configuration that is similar to stationary element 120 and includes an abutment portion 131, a pair of support portions 132a and 132b, and a connection portion 133. Positioned between the various portions 131, 132, and 133 are flexion lines 134a, 134b, and 134c that permit translating element 130 to bend between the collapsed configuration and the assembled configuration. Similarly, translating element 130 includes a pair of tabs 135a and 135b that extend from connection portion 133 in order to engage a pair of tab apertures formed in support portions 132. Translating element 130 also has inserts 137 that are received by channels 111. Inserts 137 have an L-shape that fits within channels 111, but permits translating element 130 to slide along channels 111.

Translating element 130 also includes a measurement aperture 138 formed in connection portion 133. As translating element 130 slides along base 110, translating element 130 moves in relation to scale 140. Measurement aperture 138 permits the individual to see a portion of scale 140 that is under translating element 130. When measuring the dimensions of the foot, the proper dimension for either length or width may be ascertained by reference to the portion of scale 140 that is visible through measurement aperture 138.

Scale 140 may be printed on an adhesive paper and attached to base 110. In order to ensure that scale 140 is properly positioned relative to stationary element 120, scale 140 may include an aperture that is aligned with positioning aperture 112 of base 110. Because positioning protrusion 128 of connection portion 123 engages positioning aperture 112, this arrangement ensures that scale 140 is properly positioned with respect to stationary element 120. Alternately, scale 140 may be engraved or printed directly on base 110, for example.

Traditional foot measuring devices measure the foot in accordance with one or more standard sizing systems. For example, the standard system for measuring men's feet in the United States correlates a 10.5 inch length to a size 9.5. Furthermore, width in the standard U.S. system is measured using an alphabetical scale. Scale 140 may be configured to measure the foot according to one or more standard systems or may be configured to measure the foot in accordance with a non-standard system, such as by inches or centimeters, that is developed to meet specific needs of the manufacturer. As noted in the Description of Background Art section, the size of footwear worn by an individual may vary depending upon the manufacturer that produced the footwear. By correlating scale 140 with a standard sizing system, individuals or sporting organizations may be led to believe that measurement apparatus 100 properly determines footwear sizes for a variety of manufacturers, thereby leading to improper fit. A non-standard system therefore has the benefit of ensuring that foot measurements, as determined by measurement apparatus 100, are relayed to the manufacturer, thereby providing the manufacturer with the exclusive opportunity to determine which footwear size will provide the most proper fit. In order to make this determination, the manufacturer may draw upon many sources of information, including precise knowledge of footwear dimensions and a wealth of experience regarding fit for various foot dimensions.

Suitable materials for measurement apparatus 100 may vary depending upon the projected number of individuals that may utilize measurement apparatus 100, the preferred weight of measuring apparatus 100, and the desired durability of measurement apparatus 100. In addition, a measurement apparatus 100 that is intended for use by adults may be formed of heavier, more durable materials than a measurement apparatus 100 that is intended for use by children. Although the various components of measurement apparatus 100 may be formed of materials such as steel, aluminum, cardboard, or composites of a polymer and high-strength fibers, suitable durability and weight are achieved with various conventional polymer materials.

The accuracy of measurement apparatus 100 may be compromised if damage occurs during shipping or during use, for example. A calibration device may be supplied with measurement apparatus 100 to provide a convenient method for an individual to check the accuracy of measurement apparatus 100. Generally, the calibration device may be an element with predetermined dimensions. To check the accuracy of measurement apparatus 100, the calibration device is positioned against stationary element 120. Translating element 130 is then positioned in an abutting relationship with the calibration device and the dimensions of the calibration device are ascertained. The ascertained dimensions are then compared to the predetermined dimensions. If the ascertained and predetermined correspond, measurement apparatus 100 is accurately calibrated. If, however, the measurements do not correspond, then the individual may be required to adjust foot measurements by the difference to achieve accurate results. Accordingly, the calibration device not only permits the accuracy of measurement apparatus 100 to be checked, but also provides a system by which inaccuracies may be corrected.

A register may also be utilized to record measurements of a foot. Generally, the register may be any device or method that facilitates the recording of measurements, including a pad of preprinted pages that include spaces for recording the length and width of each foot. Sporting organizations often require footwear for a plurality of individuals. Once readings are taken for a specific individual, the readings may be recorded on one of the preprinted pages of the register. The preprinted page may then be removed from the pad, thereby exposing a new preprinted page, and the printed page with the recorded readings may be given to the individual. The process may be repeated for subsequent individuals. Each individual may then utilize the recorded dimensions to independently order footwear from the manufacturer that provides a proper fit.

Measurement apparatus 200 is depicted in FIG. 5 and includes a base 210, a stationary element 220, a translating element 230, and a scale 240. The manner in which measurement apparatus 200 operates is substantially similar to measurement apparatus 100. The structure of measurement apparatus 200, however, differs from measurement apparatus 100. More particularly, the specific structure of stationary element 220 and translating element 230 differs from stationary element 120 and translating element 130, as will be described below.

The primary elements of stationary element 220 are an abutment portion 221, a single support portion 222, and a connection portion 223. In the assembled configuration, as depicted in FIGS. 5A and 5B, abutment portion 221 directly contacts the foot and provides a stationary and secure abutment for the foot when measuring length or width. Support portion 222 is connected to a top edge of abutment portion 221 and extends diagonally backward from abutment portion 221 to provide support against backward pressure from the foot. Support portion 222 includes a tab aperture 226 that engages a tab 225 extending upward from connection portion 223. Connection portion 223 provides a secure connection between stationary element 220 and base 210 and may have inserts and a positioning aperture that are similar to inserts 127 and positioning protrusion 128 of measurement apparatus 100.

Translating element 230 has a configuration that is similar to stationary element 220 and includes an abutment portion 231, a single support portions 232, and a connection portion 233. In the assemble configuration, a tab 235 that extends upward from connection portion 233 engages a tab aperture 236 in support portion 232. Translating element 230 also includes a measurement aperture 238 formed in connection portion 233. As translating element 230 slides along base 210, translating element 230 moves in relation to scale 240. Measurement aperture 238 permits the individual to see a portion of scale 240 that is under translating element 230.

Figure 5C:
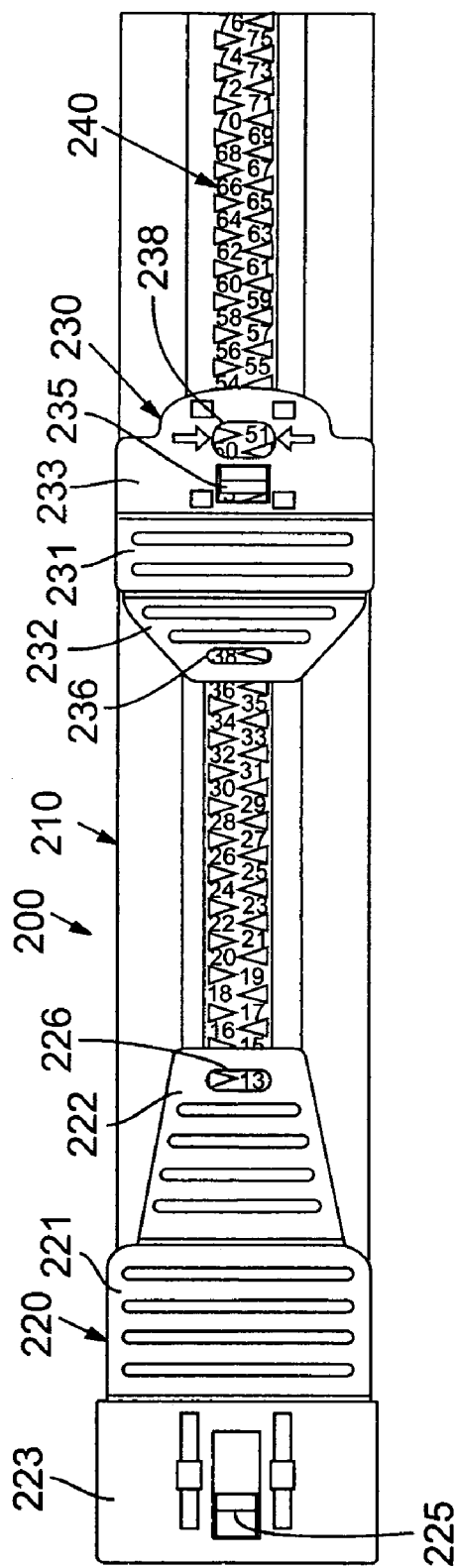
FIG. 5C is a top plan view of the second foot measurement apparatus in accordance with the present invention, the second foot measurement apparatus being in a collapsed configuration.

Measurement apparatus 200 has a collapsible configuration. By disengaging tab 225 and tab aperture 226, and disengaging tab 235 and tab aperture 236, both of stationary element 220 and translating element 230 may be placed in the collapsed configuration, as depicted in FIG. 5C. The collapsed configuration provides measurement apparatus 200 with a flat, compact configuration that is suitable for mailing, for example.

The present invention is disclosed above and in the accompanying drawings with reference to a variety of embodiments. The purpose served by the disclosure, however, is to provide an example of the various features and concepts related to the invention, not to limit the scope of the invention. One skilled in the relevant art will recognize that numerous variations and modifications may be made to the embodiments described above without departing from the scope of the present invention, as defined by the appended claims.

What is claimed is:

1. A measurement apparatus for ascertaining at least one dimension of a foot, said measurement apparatus comprising:

a base having an elongate configuration, said base defining a pair of channels extending in a direction of a length of said base, said channels being spaced inward from sides of the base;

a scale positioned on said base and between said pair of channels, said scale extending in the direction of said length of said base;

a first element that is connected to said base and extends outward from said base to form a first abutment, said first element being collapsible to place said measurement apparatus in a collapsed configuration and reduce a size of said measuring apparatus, said first element being positioned to abut a portion of the foot; and a second element that is attached to said base and extends outward from said base to form a second abutment, said second element being positioned to abut an opposite portion of the foot, said second element having at least a pair of tabs that extend into said pair of channels to movably-connect said second element to said base, and said second element defining an aperture that exposes a portion of said scale, a distance between said first element and said second element being adjustable to place said first abutment in contact with a first portion of the foot and to place said second abutment in contact with a second portion of the foot, said first portion being opposite said second portion, the at least one dimension of the foot being ascertained by reference to a position of said aperture in relation to said scale.

2. The measurement apparatus of claim 1, wherein a height of said measurement apparatus has a first value in said collapsed configuration and a second value in an assembled configuration, said first value being less than said second value.

3. The measurement apparatus of claim 1, wherein said second element is collapsible.

4. The measurement apparatus of claim 1, wherein said pair of channels extend downward and into said base.

5. The measurement apparatus of claim 4, wherein said pair of tabs extend downward from the second element to engage said pair of channels.

6. The measurement apparatus of claim 1, wherein said first element includes a connection portion and an abutment portion that are flexibly coupled together along adjoining edges, said abutment portion being rotatable with respect to said connection portion to place said measurement apparatus in one of said collapsed configuration and an assembled configuration.

7. The measurement apparatus of claim 6, wherein said first element includes an attachment mechanism for securing a position of said abutment portion with respect to said connection portion.

8. The measurement apparatus of claim 6, wherein a plane of said abutment portion is substantially orthogonal to a plane of said base when said measurement apparatus is in said assembled configuration.

9. The measurement apparatus of claim 6, wherein a plane of said abutment portion is substantially parallel to a plane of said base when said measurement apparatus is in said collapsed configuration.

10. The measurement apparatus of claim 1, wherein said second element includes a connection portion and an abutment portion that are flexibly coupled together along adjoining edges, said abutment portion being rotatable with respect to said connection portion to place said measurement apparatus in one of said collapsed configuration and an assembled configuration.

11. The measurement apparatus of claim 10, wherein said second element includes an attachment mechanism for securing a position of said abutment portion with respect to said connection portion.

12. The measurement apparatus of claim 10, wherein a plane of said abutment portion is substantially orthogonal to a plane of said base when said measurement apparatus is in said assembled configuration.

13. The measurement apparatus of claim 10, wherein a plane of said abutment portion is substantially parallel to a plane of said base when said measurement apparatus is in said collapsed configuration.

* * * * *